(12) United States Patent
Mori et al.

(10) Patent No.: US 10,151,914 B2
(45) Date of Patent: Dec. 11, 2018

(54) OPTICAL SCANNING OBSERVATION APPARATUS

(71) Applicant: OLYMPUS CORPORATION, Tokyo (JP)

(72) Inventors: Takeshi Mori, Tokyo (JP); Ken Fujinuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 214 days.

(21) Appl. No.: 15/191,801

(22) Filed: Jun. 24, 2016

(65) Prior Publication Data

US 2016/0377856 A1  Dec. 29, 2016

Related U.S. Application Data

(63) Continuation of application No. PCT/JP2014/006461, filed on Dec. 25, 2014.

(30) Foreign Application Priority Data

Dec. 25, 2013  (JP) .................................. 2013-266932

(51) Int. Cl.
*G02B 23/24* (2006.01)
*G02B 23/26* (2006.01)
(Continued)

(52) U.S. Cl.
CPC ...... *G02B 23/2469* (2013.01); *A61B 1/00172* (2013.01); *A61B 1/0638* (2013.01);
(Continued)

(58) Field of Classification Search
CPC .................................................. G02B 23/2469
See application file for complete search history.

(56) References Cited

U.S. PATENT DOCUMENTS

| 4,947,246 | A | 8/1990 | Kikuchi |
| 2013/0155215 | A1* | 6/2013 | Shimada ............ A61B 1/00172 |
| | | | 348/68 |

FOREIGN PATENT DOCUMENTS

| CN | 103347432 A | 10/2013 |
| EP | 2 436 303 A2 | 4/2012 |

(Continued)

OTHER PUBLICATIONS

Japanese Office Action dated Jun. 13, 2017 in Japanese Patent Application No. 2013-266932.
(Continued)

*Primary Examiner* — Mehrdad Dastouri
*Assistant Examiner* — Rowina J Cattungal
(74) *Attorney, Agent, or Firm* — Scully, Scott, Murphy & Presser, P.C.

(57) ABSTRACT

An optical scanning observation apparatus includes: a light source selectively emitting a plurality of illumination lights of different colors; a light emission timing controller controlling light emission timing, based on a predetermined ratio of number of light emissions of each color of the illumination light emitted from the light source; a fiber guiding the illumination light from the light source; an actuator vibratory driving the tip part of the fiber; an optical system for irradiating the illumination light emitted from the fiber; an optical detector; and a signal processor.

9 Claims, 10 Drawing Sheets

(51) Int. Cl.
*G02B 26/10* (2006.01)
*A61B 1/00* (2006.01)
*A61B 1/06* (2006.01)
*H04N 9/07* (2006.01)
*H04N 9/43* (2006.01)
*H04N 9/77* (2006.01)

(52) U.S. Cl.
CPC ..... *G02B 23/2476* (2013.01); *G02B 23/2484* (2013.01); *G02B 23/26* (2013.01); *G02B 26/10* (2013.01); *G02B 26/103* (2013.01); *H04N 9/07* (2013.01); *H04N 9/43* (2013.01); *H04N 9/77* (2013.01); *A61B 1/00036* (2013.01); *H04N 2209/044* (2013.01)

(56) References Cited

FOREIGN PATENT DOCUMENTS

| | | | | |
|---|---|---|---|---|
| EP | 2 452 611 | A1 | | 5/2012 |
| EP | 2452611 | A1 * | 5/2012 | ........... A61B 1/0638 |
| EP | 2 556 790 | A1 | | 2/2013 |
| EP | 2556790 | A1 * | 2/2013 | ........... A61B 1/0638 |
| JP | 2002-122794 | A | | 4/2002 |
| JP | 2010-042128 | A | | 2/2010 |
| JP | 2011-125598 | A | | 6/2011 |
| WO | WO 2012/132754 | A1 | | 10/2012 |

OTHER PUBLICATIONS

Chinese Office Action dated May 19, 2017 in Chinese Patent Application No. 201480070945.9.
Chinese Office Action dated Jan. 19, 2018 in Chinese Patent Application No. 201480070945.9.
International Search Report dated Mar. 31, 2015 issued in PCT/JP2014/006461.
Extended Supplementary European Search Report dated Oct. 13, 2017 in European Patent Application No. 14 87 5488.0.

* cited by examiner

FIG. 5A  LASER R
FIG. 5B  LASER G
FIG. 5C  LASER B
FIG. 5D  LASER COUPLING
FIG. 5E  DETECTOR OUTPUT
FIG. 5F  PHOTORECEPTIVE PIXEL

FIG. 6A  LASER R
FIG. 6B  LASER G
FIG. 6C  LASER B
FIG. 6D  LASER MIXING
FIG. 6E  DETECTOR OUTPUT
FIG. 6F  PHOTORECEPTIVE PIXEL

OPTICAL SCANNING OBSERVATION APPARATUS

CROSS-REFERENCE TO RELATED APPLICATION

The present application is a Continuing Application based on International Application PCT/JP2014/006461 filed on Dec. 25, 2014, which in turn claims priority to Japanese Patent Application No. 2013-266932 filed on Dec. 25, 2013, the entire disclosure of these earlier applications being incorporated herein by reference.

TECHNICAL FIELD

The present disclosure relates to an optical scanning observation apparatus which optically scans an object through vibration of an optical fiber.

BACKGROUND ART

There has been hitherto known a medical probe for observing an object using pulse lights of a plurality of different wavelengths irradiated from a light source, the probe having: a light guide unit guiding the pulse light incident from the light source to emit the light to the object; and an optical delay unit for giving, with respect to reflected pulse light from the object irradiated with the emitted pulse light, a predetermined delay time that is different for each wavelength, the probe outputting the pulse light which is given the delay time to a predetermined photodetector (see, for example, Patent Literature 1). This configuration is considered to allow for reducing to one the number of the optical detectors.

Figures 10A, 10B, 10C:
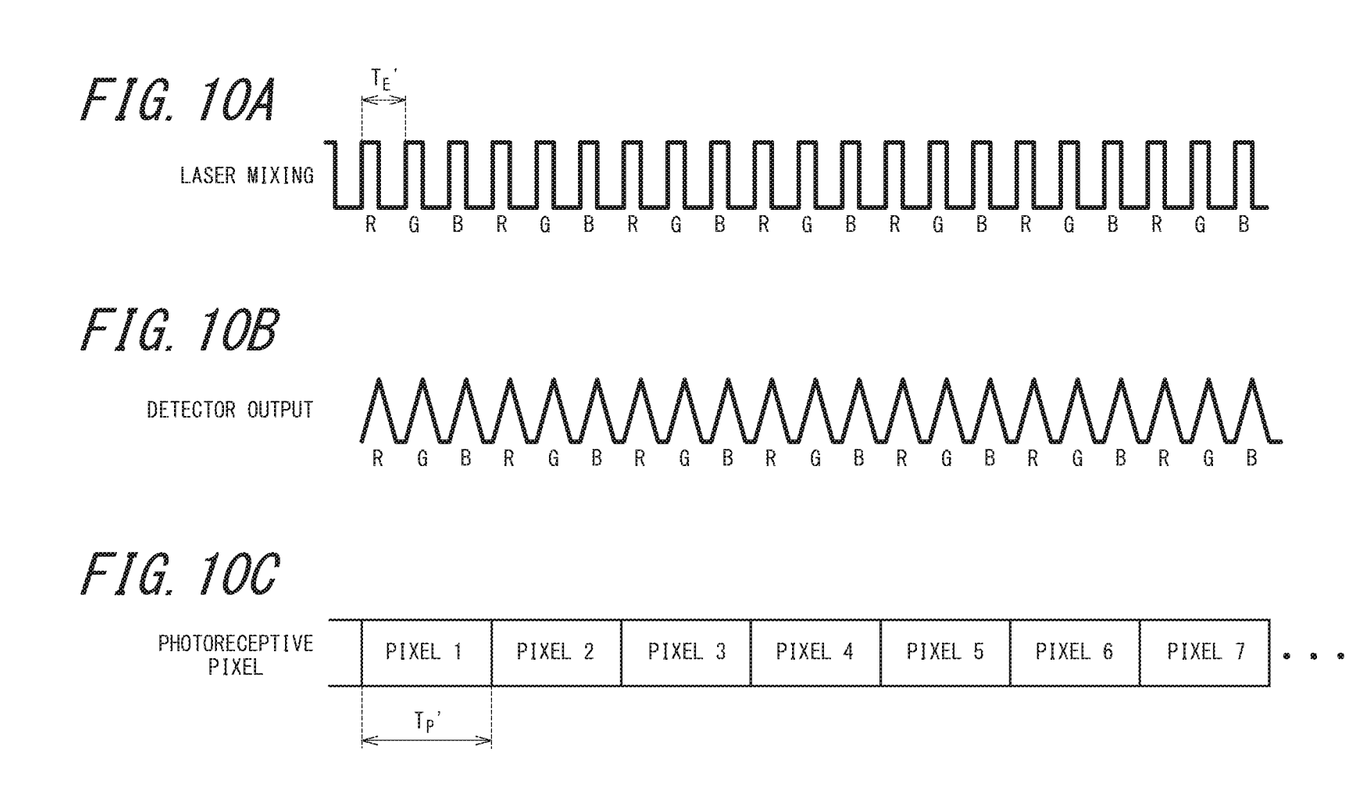
FIGS. 10A-10C are views for illustrating an example of conventional light emission timing.

Another conceivable technique that allows for reducing to one the number of optical detectors may involve sequentially switching lasers of red, green, blue along with a sampling rate as illustrated in FIGS. 10A-10C for example, so as to sequentially irradiate pulse light of each color onto the object.

CITATION LIST

Patent Literature

PTL 1: JP201042128A

SUMMARY

An optical scanning observation apparatus to be provided includes:

a light source selectively emitting a plurality of illumination lights of different colors;

a light emission timing controller controlling light emission timing, based on a predetermined ratio of number of light emissions of each color of the illumination light emitted from the light source;

a fiber guiding the illumination light from the light source and emitting the illumination light from a tip part of the fiber, the tip part being oscillatably supported;

an actuator vibratory driving the tip part of the fiber;

an optical system for irradiating the illumination light emitted from the fiber toward an object;

an optical detector detecting detection light obtained from the object via the irradiating of the illumination light and converting the detection light obtained from the object into an electric signal; and a signal processor generating an image signal, based on the electric signal from the optical detector.

The light emission timing controller may preferably define the predetermined ratio of number of light emissions of a color having high contribution to image quality, to be higher than the predetermined ratio of number of light emissions of the rest of the colors.

Here, the image quality may include image brightness or contrast or bandwidth, or any combination thereof.

The optical scanning observation apparatus may further include an object color detector for extracting, based on the image signal generated by the image generator, a color having high contribution to image brightness of an image to be generated by the image signal, in which the light emission timing controller may control, based on the output from the object color detector, the predetermined ratio of number of light emissions for each color of the illumination light from the light source.

BRIEF DESCRIPTION OF DRAWINGS

In the accompanying drawings:

FIGS. 4A and 4B each illustrate the actuator and the oscillation part of the illumination optical fiber of FIG. 3, in which FIG. 4A is a side view thereof.

FIGS. 9A to 9C are diagrams for illustrating a modified example of the actuator of FIGS. 4A and 4B, in which

DESCRIPTION OF EMBODIMENTS

The following describes Embodiments disclosed herein, with reference to the drawings.

Embodiment 1

Figure 1:
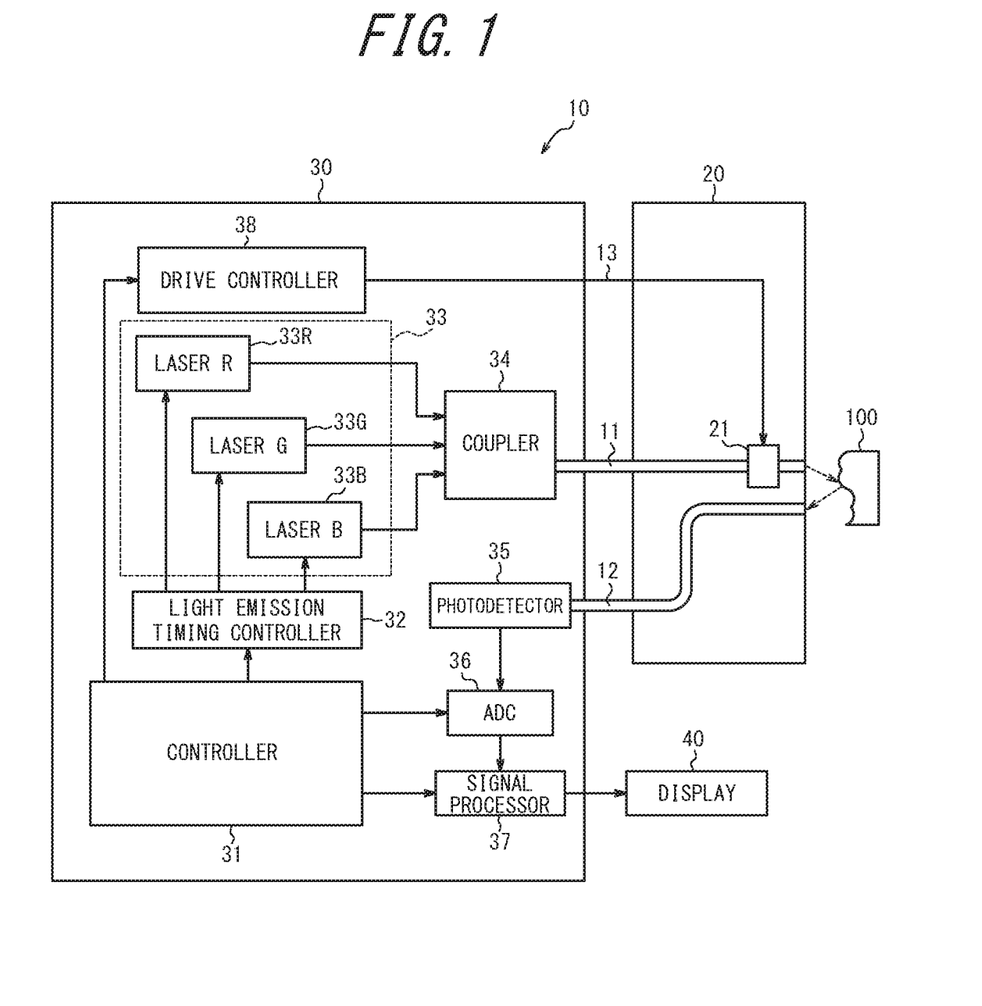
FIG. 1 is a block diagram illustrating a schematic configuration of an optical scanning endoscope apparatus as an example of the disclosed optical scanning observation apparatus according to Embodiment 1.

Embodiment 1 of the disclosed optical scanning observation apparatus is described with reference to FIGS. 1 to 6F. FIG. 1 is a block diagram illustrating a schematic configuration of an optical scanning endoscope apparatus as an example of the disclosed optical scanning observation apparatus according to Embodiment 1. FIG. 1 shows an optical scanning endoscope apparatus 10, which includes a scope 20, a control device body 30, and a display 40.

First, a configuration of the control device body 30 is described. The control device body 30 includes: a controller 31 for controlling throughout the optical scanning endoscope apparatus 10; a light emission timing controller 32; lasers 33R, 33G, 33B; a coupler 34; a drive controller 38; a photodetector 35 (optical detector); an analog-digital converter (ADC) 36; and a signal processor 37.

The emission timing controller 32 controls, based on the control signal from the controller 31, light emission timings of the lasers 33R, 33G, 33B each emitting red (R), green (G), and blue (B) laser illumination lights, respectively. Here, the light emission timings are controlled such that the ratio of number of light emissions among the respective illumination light colors is obtained as a set value. In Embodiment 1, the value of the ratio of number of light emissions among the respective illumination light colors may be set at an optional timing by a user through input unit (not shown) or set in advance at the time of shipment of the optical scanning endoscope apparatus 10, and stored in a memory (not shown) readable and writable by the controller 31. The light emission timings are set such that illumination lights in the different colors may each be emitted at every fixed time interval (light emission cycle $T_E$) in the light emission sequence (for example, in the order of R, G, B, G) determined based on the set value of the ratio of number of light emissions among the different illumination light colors (for example, 1:2:1 in the order of R, G, B).

The lasers 33R, 33G, 33B constitute a light source 33 for selectively emitting a plurality of illumination lights of different colors (three colors of R, G, and B in Embodiment 1). Here, "selectively emitting a plurality of illumination lights of different colors" specifically refers to emitting illumination light of any one of the colors selected by the light emission timing controller 32 at a timing selected by the light emission timing controller 32. Exemplary lasers that can be used as the lasers 33R, 33G, 33B may include, for example, a diode-pump solid state (DPSS) laser and a laser diode.

Here, in the disclosure, the "light emission cycle $T_E$" refers to the emission cycle of illumination light sequentially emitted from the light source 33, rather than the light emission cycle of each of the lasers 33R, 33G, 33B constituting the light source 33.

Laser illumination lights emitted from the lasers 33R, 33G, 33B travel through optical paths coaxially combined by the coupler 34, and are made incident, as illumination light, onto an illumination optical fiber 11 (fiber) as a single mode fiber. The coupler 34 may be formed using, for example, a dichroic prism.

The lasers 33R, 33G, 33B and the coupler 34 may be stored in a separate casing different from the control body 30, the separate casing being connected to the control device body 30 via a signal line.

The illumination light that has been incident onto the illumination optical fiber 11 from the coupler 34 is guided to the tip part of the scope 20 and irradiated toward an object 100. At this time, the drive controller 38 of the control device body 30 vibratory drives an actuator 21 of the scope 20, to thereby vibratory drive the tip part of the illumination optical fiber 11. In this manner, the illumination light emitted from the illumination optical fiber 11 is two-dimensionally scanned, for example, in a spiral manner, on the observation surface of the object 100. The object 100 irradiated by the illumination light provides detection light including reflected light and scattered light, which are received at the tip end of a detection optical fiber bundle 12 formed of multimode fibers and guided to the control device body 30 through the scope 20.

The photodetector 35 detects, for every light emission cycle $T_E$ of the light source 33, detection light obtained via the detection optical fiber bundle 12 from the object 100 irradiated with illumination light of any color of R, G, or B, and outputs an analog signal (electric signal) band-limited for the color.

The ADC 36 converts the analog signal from the photodetector 35 into a digital signal (electric signal), and outputs the signal to the signal processor 37.

The signal processor 37 sequentially stores, in a memory (not shown), each digital signal which is input from the ADC 36 for every light emission cycle $T_E$ and corresponds to each color, in association with the light emission timing and the scanned position. Information on the light emission timing and the scanning position is obtained from the controller 31. The controller 31 calculates information on the scanning position on the scanning path, based on such information as the amplitude and phase of a vibration voltage applied by the drive controller 38. Then, after the scan is completed or during the scan, the signal processor 37 subjects each digital signal input from the ADC 36 to necessary image processing such as enhancement processing, γ processing, and interpolation processing, to thereby generate an image signal, and displays an image of the object 100 on the display 40.

Figure 2:
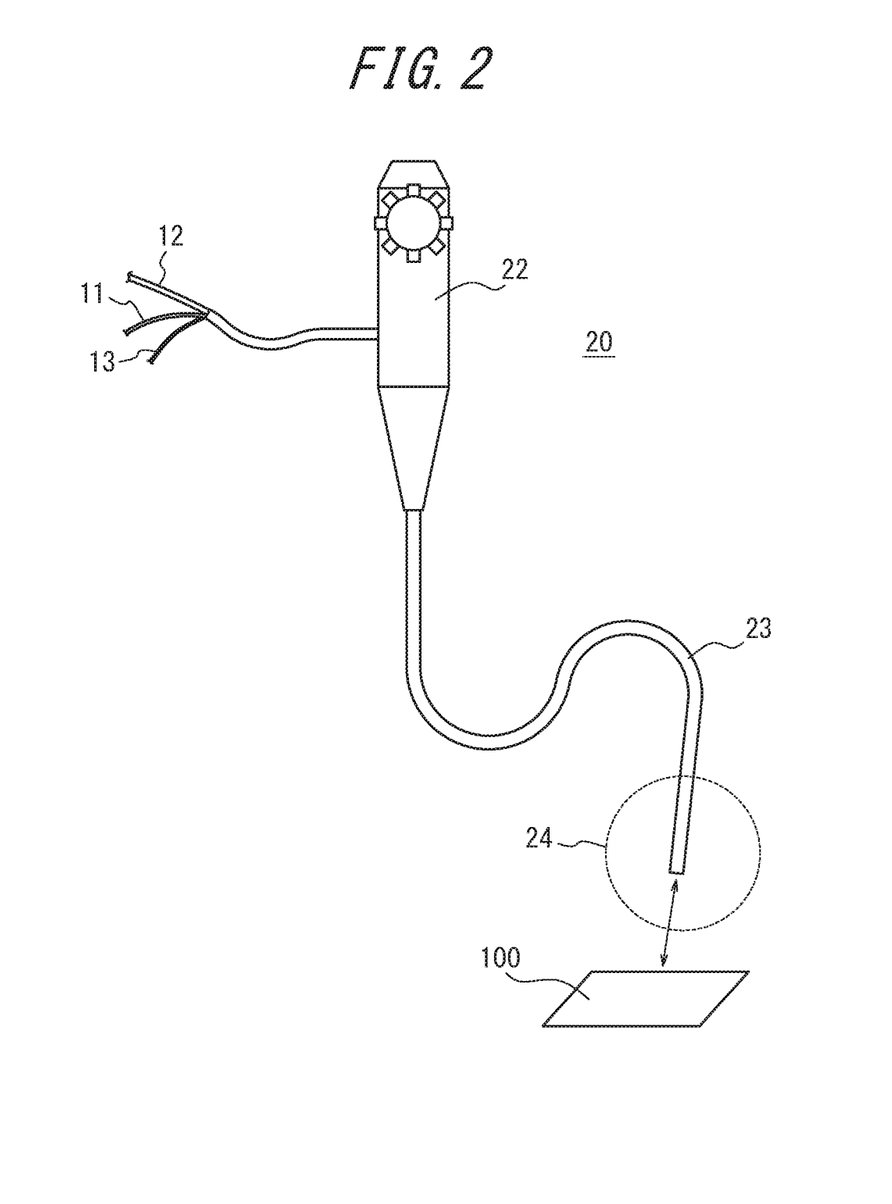
FIG. 2 is an overview schematically illustrating the scope of FIG. 1.

Next, a configuration of the scope 20 is described. FIG. 2 is an overview schematically illustrating the scope 20. The scope 20 includes an operation portion 22 and an insertion portion 23. The illumination optical fiber 11, the detection optical fiber bundle 12, and a wiring cable 13 from the control device body 30 are each connected to the operation portion 22. The illumination optical fiber 11, the detection optical fiber bundle 12, and the wiring cable 13 pass through inside the insertion portion 23, and extend to the tip part 24 (enclosed by the dashed line of FIG. 2) of the insertion portion 23.

Figure 3:
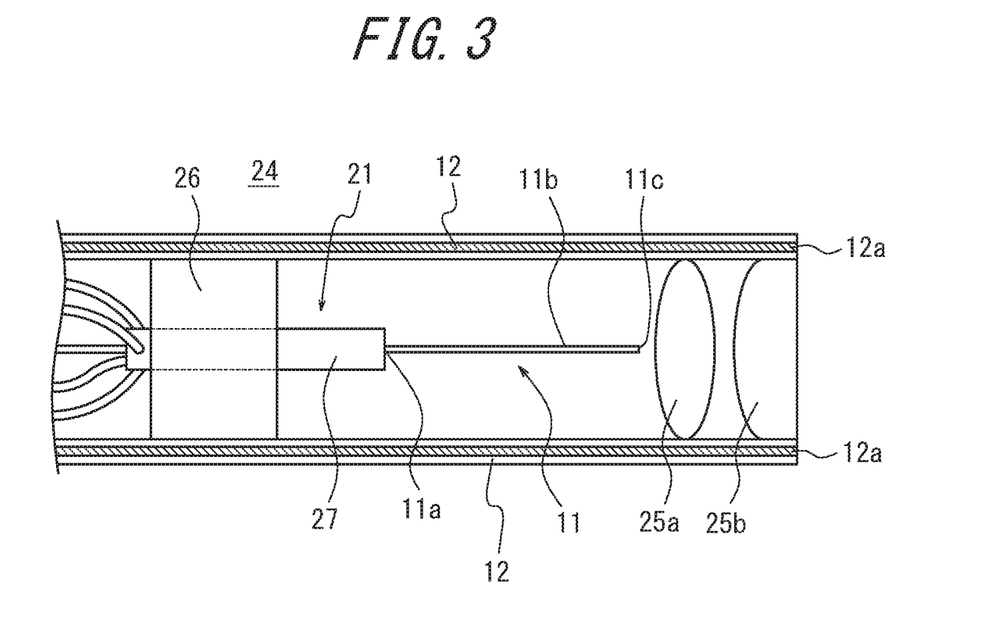
FIG. 3 is a sectional view of the tip part of the scope of FIG. 2.

FIG. 3 is an enlarged sectional view of the tip part 24 of the insertion portion 23 of the scope 20 of FIG. 2. The tip part 24 of the insertion portion 23 of the scope 20 is configured by including: the actuator 21; a projection lenses 25a, 25b (optical system); the illumination optical fiber 11 passing through the center part; and the detection optical fiber bundle 12 passing through the circumferential part.

The actuator 21 vibratory drives a tip part 11c of the illumination optical fiber 11. The actuator 21 is configured by including: an actuator tube 27 fixed inside the insertion portion 23 of the scope 20 through an attachment ring 26; and a fiber holding member 29 and piezoelectric elements 28a to 28d (see FIGS. 4A and 4B) disposed inside the actuator tube 27. The illumination optical fiber 11, which is supported by the fiber holding member 29, has an oscillation part 11b oscillatably supported, the oscillation part 11b being defined between an fixed end 11a supported by the fiber holding member 29 and the tip part 11c. Meanwhile, the detection optical fiber bundle 12 is disposed so as to pass through the circumferential part of the insertion portion 23 to extend to the tip end of the tip part 24. Further, the detection optical fiber bundle 12 includes a detection lens, which is not shown, at the tip part of each fiber.

Further, the projection lenses 25a, 25b and the detection lens are disposed at an extreme tip of the tip part 24 of the insertion portion 23 of the scope 20. The projection lenses 25a, 25b are configured such that laser illumination light emitted from the tip part 11c of the illumination optical fiber 11 is irradiated on the object 100 so as to be substantially converged thereon. Further, the detection lens is disposed to take in the laser detection light that has been reflected, scattered, or refracted by the object 100 (detection light that has interacted with the object 100) after being converged on the object 100, so as to converge and couple the laser detection light to the detection optical fiber bundle 12 disposed behind the detection lens. Here, one projection lens or a plurality of other lenses may constitute the projection lens system, without being limited to the two-lens configuration.

Figure 4A:
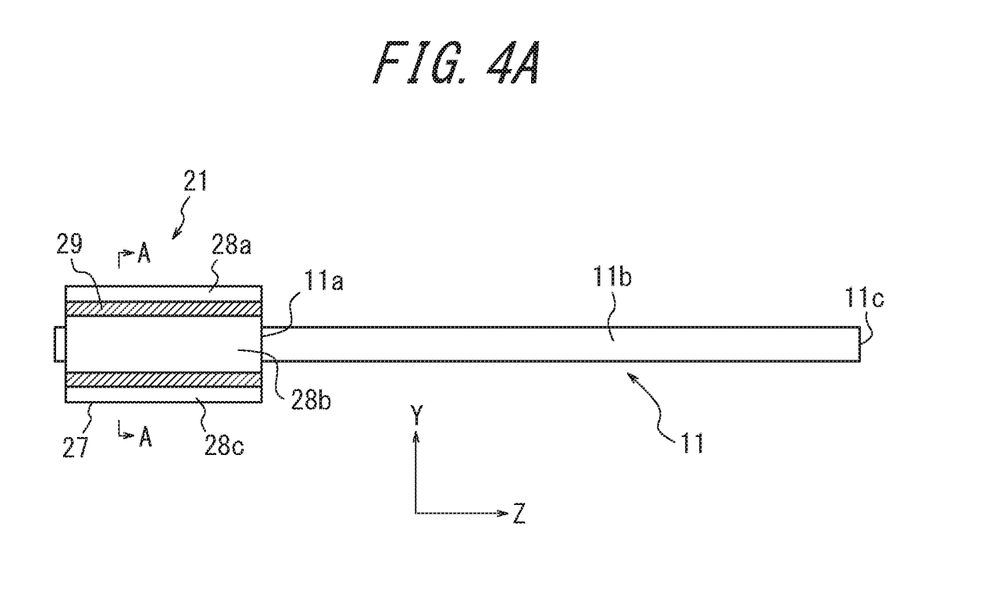
Figure 4B:
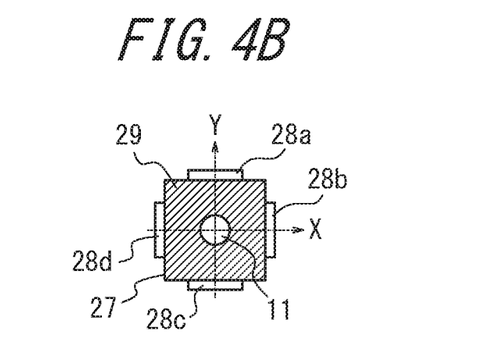
FIG. 4B is a sectional view taken along the line A-A of FIG. 4A.

FIG. 4A illustrates a vibratory driving mechanism of the actuator 21 of the optical scanning endoscope apparatus 10 and the oscillation part 11b of the illumination optical fiber 11, and FIG. 4B is a sectional view taken along the line A-A of FIG. 4A. The illumination optical fiber 11 penetrates the center of the fiber holding member 29 in a prism shape, and is fixedly held by the fiber holding member 29. The fiber holding member 29 has four side faces each facing the ±Y directions and the ±X directions, respectively, of which two side faces of the fiber holding member 29 facing the ±Y directions have a pair of the Y-direction driving piezoelectric elements 28a, 28c fixed thereon, and two side faces of the fiber holding member 29 facing the ±X directions have a pair of the X-direction driving piezoelectric elements 28b, 28d fixed thereon.

The piezoelectric elements 28a to 28d are each connected with the wiring cable 13 from the drive controller 38 of the control device body 30, and driven by voltage applied by the drive controller 38.

Voltages to be applied between the X-direction piezoelectric elements 28b and 28b are constantly inverted with plus and minus but equal to each other in magnitude. Similarly, voltages to be applied between the Y-direction piezoelectric elements 28a and 28c are constantly inverted with plus and minus but equal to each other in magnitude. Of the piezoelectric elements 28a, 28d disposed as being opposite to each other across the fiber holding member 29, one is extended while the other is contracted in an alternating manner to deflect the fiber holding optical fiber 29, which may be repeated to cause vibration in the X direction. Vibration in the Y direction is similarly caused.

The drive controller 38 applies vibration voltages of the same frequency or applies vibration voltages of different frequencies to the X-direction driving piezoelectric elements 28b, 28d and the Y-direction driving piezoelectric elements 28a, 28c, to thereby vibratory drive the piezoelectric elements 28a to 28d. When the Y-direction driving piezoelectric elements 28a, 28c and the X-direction driving piezoelectric elements 28b, 28d are each vibratory driven, the oscillation part 11b of the illumination optical fiber 11 of FIG. 3 or 4 is vibrated so as to deflect the tip part 11c, and thus, laser illumination light emitted from the tip part 11c is sequentially scanned (for example, in a spiral manner) on the surface of the object 100.

Figure 5A:
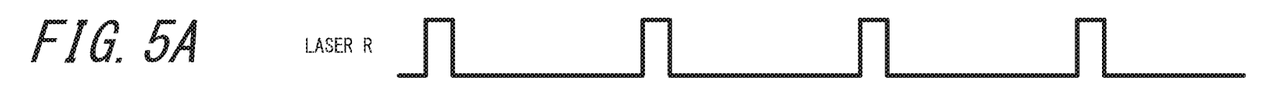
FIGS. 5A-5F illustrate an example of the light emission timing of the light source.
Figure 5B:
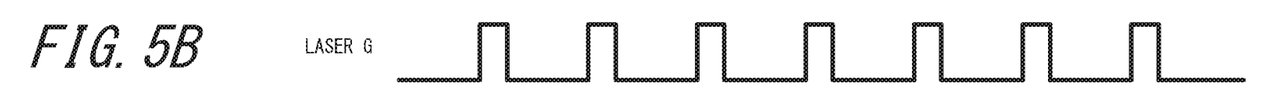
Figure 5C:
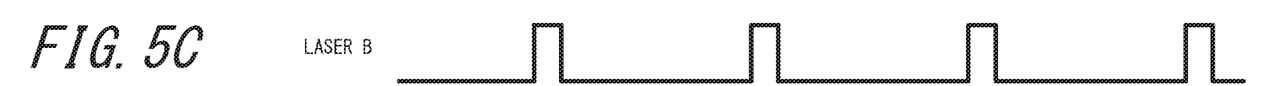
Figure 5D:
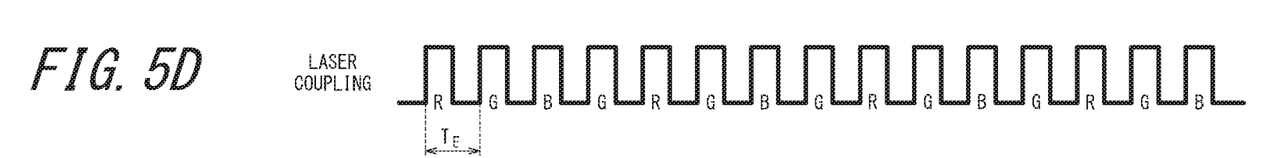
Figure 5E:
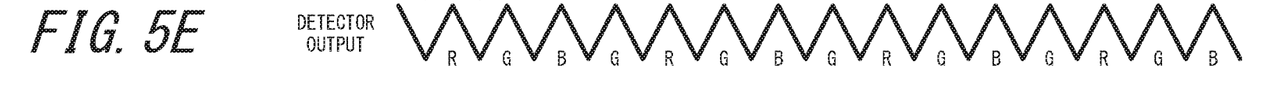

Next, an operation of the optical scanning endoscope apparatus 10 is described with reference to FIGS. 5A-5F, mainly about the processing in the light emission timing controller 32 and in the signal processor 37. FIGS. 5A-5F are for illustrating an example of the light emission timing of the light source 33, in which the time sequence is from left to right of the drawing. In the example of FIGS. 5A-5F, the ratio of number of light emissions among the illumination lights of R, G, B is defined as 1:2:1, and illumination lights are emitted in the order of R, G, B, G. The light emission timing controller 32 controls, in accordance with the control signal from the controller 31, the light emission timings of the lasers 33R, 33G, 33B in the order of R, G, B, G for every light emission cycle $T_E$. The light emission timing of the lasers 33R, 33G, 33B at this time are shown in FIGS. 5A to 5C, the output of the coupler 34 is shown in FIG. 5D, and the output of the photodetector 35 is shown in FIG. 5E.

Figure 5F:
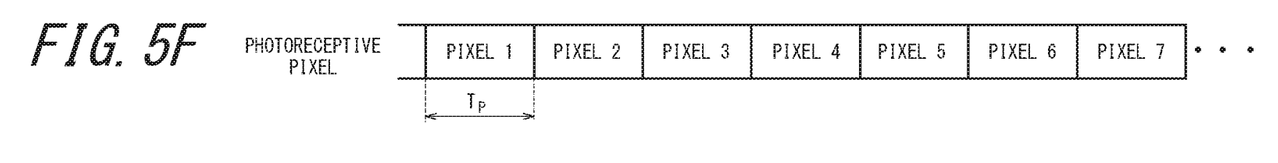
Figures 6A, 6B, 6C:
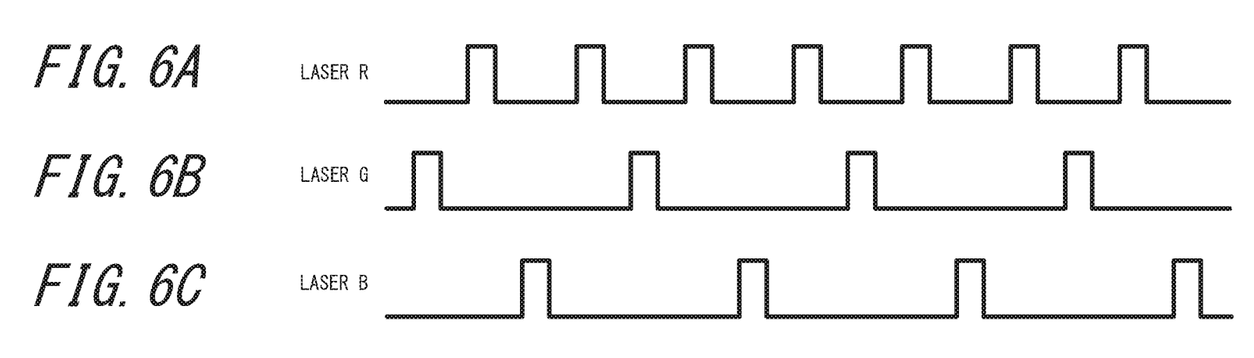
FIGS. 6A-6F illustrate another example of the light emission timing of the light source.
Figure 6D:
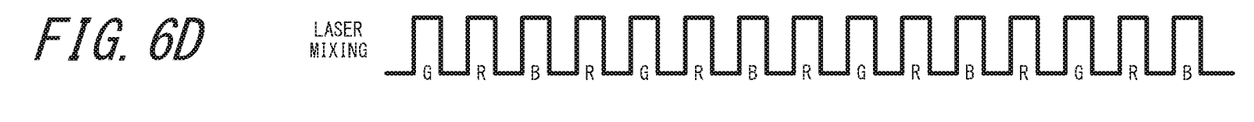
Figure 6E:
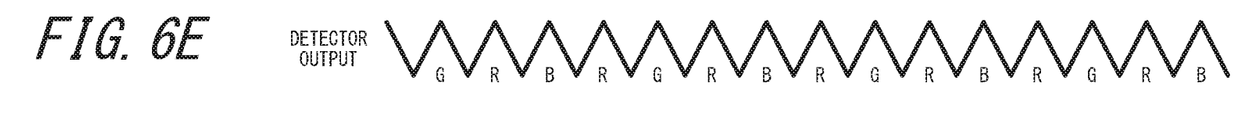
Figure 6F:
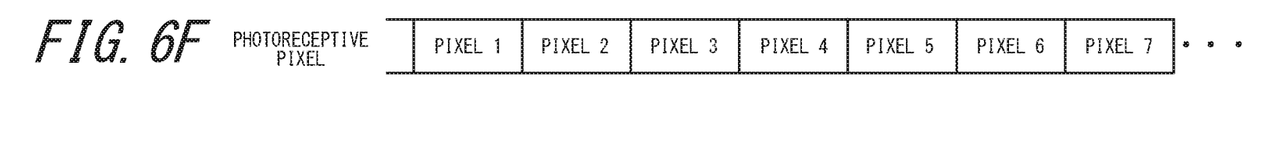

The signal processor 37 generates image signals, as illustrated in FIG. 5F, based on electric signals for two colors (of R and G, or B and G) sequentially input from the photodetector 35 via the ADC 36, and outputs the signal to the display 40. At this time, absent color for each pixel may desirably be interpolated with the aid of neighboring pixels. For example, electric signals each associated with R and G, respectively, are input to a pixel 5 of FIG. 5F, and thus, the absent color B is interpolated based on the neighboring pixels by a publicly-known method. Through such interpolation processing, image signal components of three colors of RGB can be incorporated per one pixel, which improves the image definition. Here, the "neighboring pixels" herein refer to neighboring pixels along the scanning trajectory of the tip part 11c of the illumination optical fiber 11, or neighboring pixels to be found when generating image signals to be output to the display 40.

As described above, in the example of the light emission timings of FIGS. 5A-5F, illumination light is emitted twice per one pixel (number of light emission pulses), which is ⅔ of the three times in the conventional example of FIGS. 10A-10C. This configuration reduces to ⅔ current consumption for laser emission, provided that the pulse width is supposedly the same as that of the conventional example of FIGS. 10A-10C. On the other hand, it is generally known that the color G highly contributes to brightness (luminance) of the image as compared with the other colors (R, B), while the color B less contributes to brightness as compared with the other colors (R, G). Accordingly, in a case where the object includes not so many R and B components in particular, the ratio of number of light emissions of G may be set higher as compared to the rest of the colors as in this example, to thereby obtain sufficiently excellent image resolution (definition) while reducing current consumption.

Further, in the examples of FIGS. 5A-5F, the light emission cycle $T_E$ is ½ of a cycle (pixel cycle) $T_P$ at which electric signals for one pixel are input. On the other hand, in the conventional example of FIGS. 10A-10C, the light emission cycle $T_E'$ is ⅓ of the pixel cycle $T_P'$. Accordingly, suppose that the pixel cycles $T_P$, $T_P'$ are the same, the light emission cycle $T_E$ in the example of FIGS. 5A-5F becomes longer than the light emission cycle $T_E'$ in the conventional example of FIGS. 10A-10C, which allows the signal band width to be narrowed in the photodetector 35, to thereby reduce noise resulting from superposition of signals of different colors potentially caused by ringing phenomenon. On the other hand, suppose the light emission cycles $T_E$, $T_E'$ are the same, the pixel cycle TP in the example of FIGS. 5A-5F becomes shorter than the pixel cycle TP' in the conventional example of FIGS. 10A-10C, which can improve image resolution.

Meanwhile, in a case where the image depicts an object having particularly many R components (such as an image of the inside of a blood vessel), the ratio of number of light emissions of R may desirably be increased to be higher as compared to the other colors (G, B) as in another example of FIGS. 6A-6F because the color R highly contributes to image brightness. In the example of FIGS. 6A-6F, the ratio of number of light emissions of R, G, B is defined as 2:1:1, and illumination lights are emitted in the order of G, R, B, R. With this configuration, sufficiently excellent image resolution can be obtained while reducing current consumption to ⅔ of that in the conventional practice.

Similarly, in a case where the image depicts an object having particularly many B components (such as an image of a part stained with a dye of blue B so as to facilitate recognition of the inflamed side site), the ratio of number of light emissions of B may desirably be increased to be higher as compared to the other colors (R, G) because the color B highly contributes to brightness of the image. Here, without being limited to the aforementioned example which increases the light emission ratio of a color having high contribution to brightness, any color may be selected to be increased in light emission ratio thereof. For example, a highly contrasted color in the captured image or a color having frequency components across a wide bandwidth may be selected, or the color may be determined depending on the combination of the aforementioned image qualities.

As described above, in view of reducing the current consumption while suppressing degradation in image resolution, the ratio of number of light emissions of each color may desirably be determined in such a manner that a color with the highest contribution to image brightness may have a higher ratio of number of light emissions than the rest of the colors.

According to Embodiment 1, current consumption can be reduced while suppressing degradation in image resolution.

Embodiment 2

Figure 7:
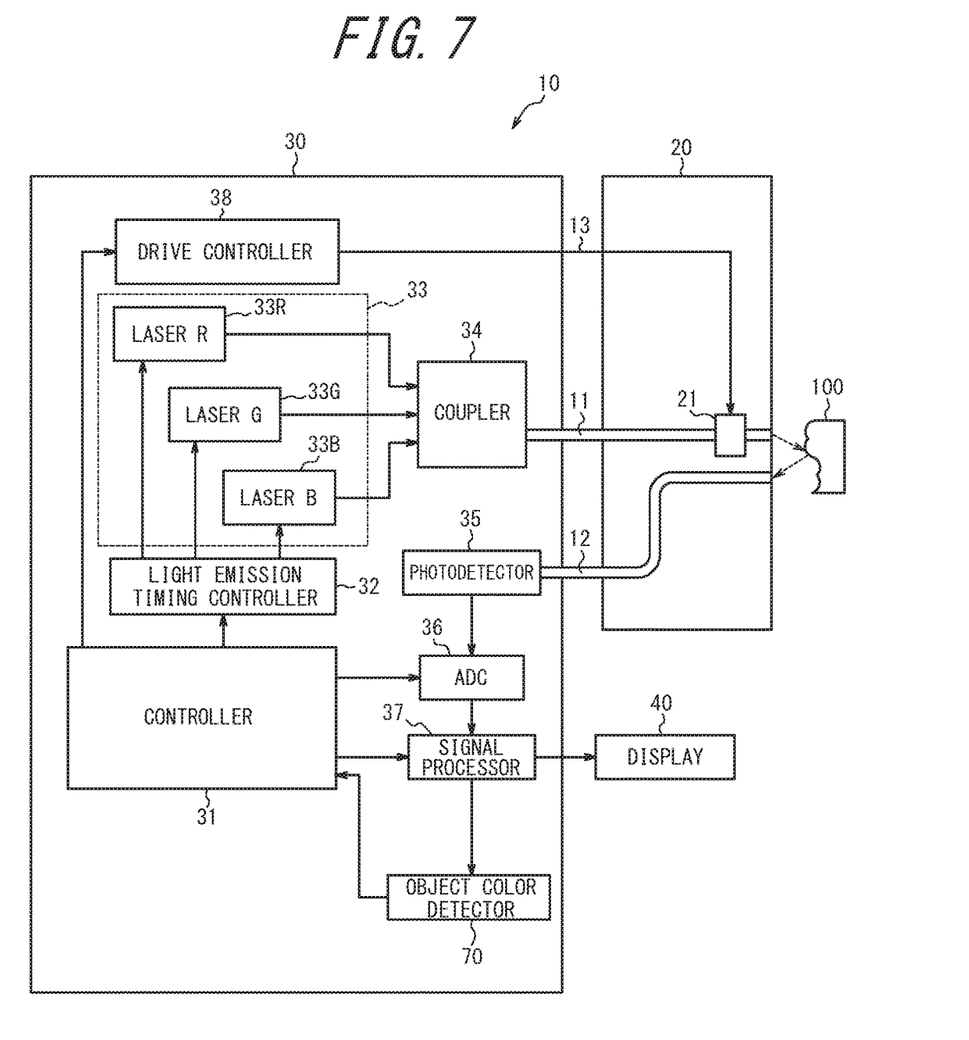
FIG. 7 is a block diagram illustrating a schematic configuration of an optical scanning endoscope apparatus as an example of the disclosed optical scanning observation apparatus according to Embodiment 2.

Embodiment 2 of the disclosed optical scanning observation apparatus is described with reference to FIGS. 7 and 8. FIG. 7 is a block diagram illustrating a schematic configuration of an optical scanning endoscope apparatus as an example of the disclosed optical scanning observation apparatus according to Embodiment 2. Embodiment 2 is different from Embodiment 1 in that the control device body 30 further includes an object color detector 70, and thus detailed description of the rest of the configuration is omitted.

In Embodiment 1, the ratio of number of light emissions of each color of illumination light from the light source 33 is set by the user through an input unit at an optional timing or may be set in advance at the time of shipment of the optical scanning endoscope apparatus, while in Embodiment 2, the ratio of number of light emissions is automatically optimized by the object color detector 70 depending on the object. This configuration saves user's trouble of resetting the ratio of number of light emissions every time observing a different object, which thus improves user convenience as compared with Embodiment 1.

As illustrated in FIG. 7, the object color detector 70 is connected to the signal processor 37 and to the controller. The object color detector 70 extracts, based on an image signal generated by the signal processor 37, a color with high contribution to image brightness (luminance), determines the ratio of number of light emissions of each color such that the extracted color has the higher ratio of number of light emissions than the rest of the colors, and notifies the controller 31 of the ratio of number of light emissions thus determined.

Next, an operation of the optical scanning endoscope apparatus 10 is described with reference to FIG. 8, mainly about the processing in the light emission timing controller 32, in the signal processor 37, and in the object color detector 70. FIG. 8 is a flow chart illustrating the processing in the object color detector 70. In Embodiment 2, the emission timing of FIGS. 5A-5F is set as the initial setting, in which the ratio of number of light emissions among the illumination lights of R, G, B is defined as 1:2:1. The initial setting is set in advance, for example, through the user input or through an input at the time of shipment of the optical scanning endoscope apparatus 10.

When image signals of an arbitrary image are input from the signal processor 37 (Step S1, Yes), the object color detector 70 calculates an average level of the image signal values for the respective colors of R, G, B (Step S2). Steps S1 to S2 may process each image signal involved throughout the one image, or may process only some image signals involved in a part (for example, the region of interest, such as the central region) of the one image.

Next, the object color detector 70 multiplies the average level of the image signal values of the respective colors calculated in Step S2 with a coefficient related to luminance of each color (Step S3). The coefficient is stored in a memory (not shown) in advance, an example of which is available as a coefficient generally used for calculating the luminance signal of a display (coefficient of 0.3 for R, 0.59 for G, and 0.11 for B).

Next, the object color detector 70 compares the product values obtained in Step S3 (Step S4), extracts a color corresponding to the maximum value as a color having highest contribution to brightness (luminance) of the image (Steps S5 to S7), and sets the ratio of number of light emissions of the color two times higher than the rest of the colors (Steps S8 to S10). The ratio of number of light emissions set by the object color detector 70 is conveyed to the controller, which updates the set value of the ratio of number of light emissions held in the controller 31. Then, the light emission timing controller 32 controls, in response to a control signal from the controller 31, the ratio of number of light emissions for each color of the illumination light from the light source 33, according to the ratio of number of light emissions determined by the object color detector 70. Accordingly, in an exemplary case where the object color detector 70 has extracted G as the color having highest contribution to image luminance (Step S5, Yes), the ratio of number of light emissions among R, G, B is maintained as 1:2:1 (Step S8), and the light emission timing controller 32 continues to control the light source 33 in line with the light emission timing of FIGS. 5A-5F. Meanwhile, in a case where the object color detector 70 has extracted R as the color having highest contribution to image luminance (Step S6, Yes), the ratio of number of light emissions among R, G, B is changed to 2:1:1, and the light emission timing controller 32 then controls the light source 33 in line with the light emission timing of FIGS. 6A-6F.

According to Embodiment 2, the ratio of number of light emissions is automatically optimized, saving user's trouble of resetting the ratio of number of light emissions every time observing a different object, which thus improves user convenience.

The process of Step S8 may be performed at an optional timing during the observation (scan) of the object; for example, the process may be performed only at the start of observation or may be performed periodically during observation. When the process of FIG. 8 is performed during observation, Step S1 may wait until the user inputs a process start instruction via the input unit (not shown). In this case, when the user inputs the process start instruction in Step S1, the object color detector 70 performs Step S2 and the steps that follow Step S2.

Figure 8:
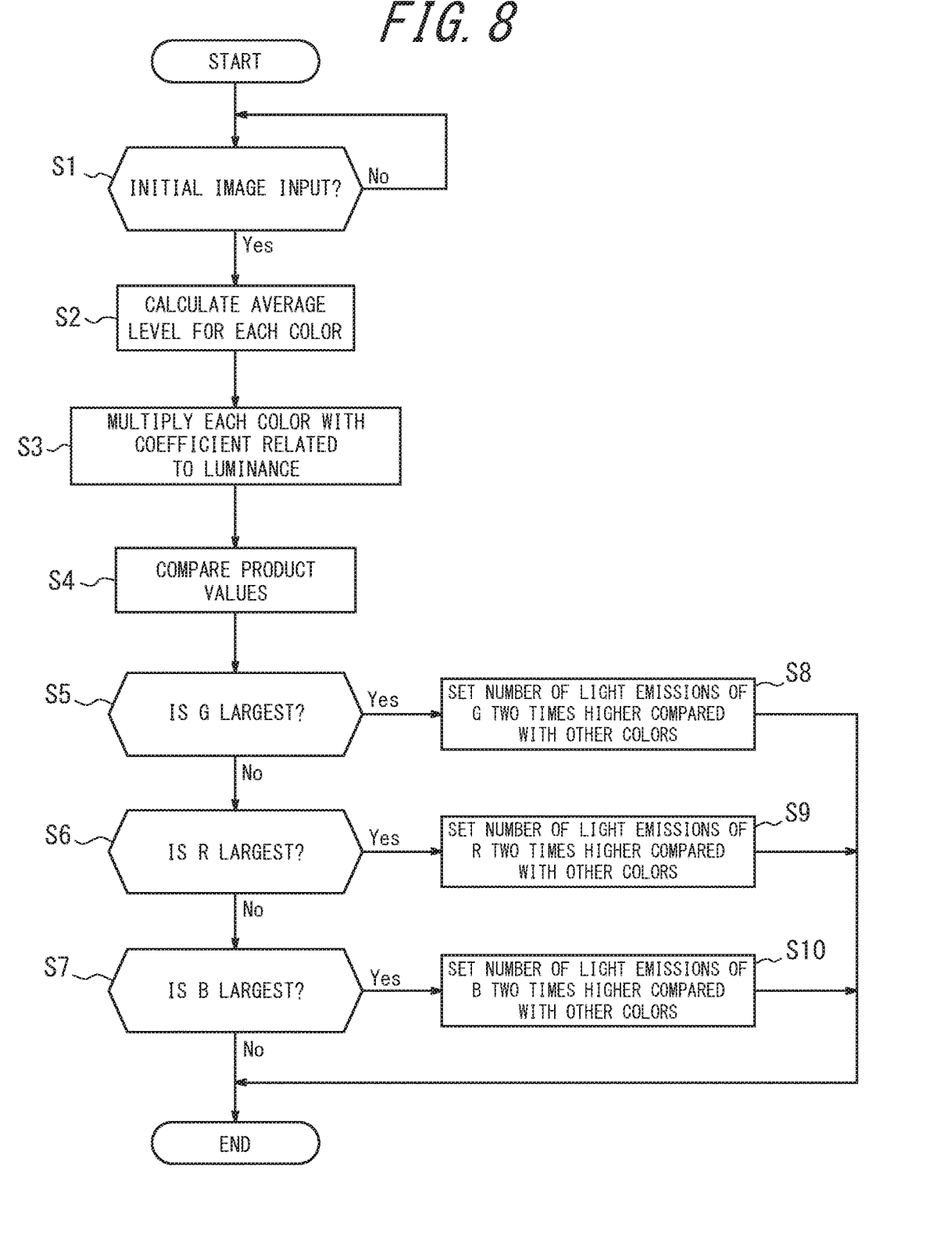
FIG. 8 is a flow chart illustrating the processing in the object color detector of FIG. 7.

As the initial setting of the process of FIG. 8, an optional light emission timing may be set, such as the light emission timing as illustrated in the example of FIGS. 10A-10C where the ratio of number of light emissions among R, G, B is 1:1:1.

In Steps S5 to S8 of FIG. 8, the ratio of number of light emissions of each color may be set to an optional value so that a color of highest contribution to image brightness has the ratio of number of light emissions higher than the rest of the colors. For example, the ratio of number of light emissions of each color may be set (for example, to 3:2:1) so as to be proportional to the product value of each color calculated in Step S3, or the product values of the respective values may be aligned in the same descending order as the ratio of number of light emissions of each color. Further, as in Embodiment 1, without being limited to the aforementioned example which increases the light emission ratio of a color having high contribution to brightness, any color may be selected to be increased in light emission ratio thereof. For example, a highly contrasted color in the captured image or a color having frequency components across a wide bandwidth may be selected, or the color may be determined depending on the combination of the aforementioned image qualities.

In Embodiments 1 and 2, the optical scanning endoscope apparatus 10 may include any light source without being limited to the configuration which includes the lasers 33R, 33G, 33B, as long as it selectively emits a plurality of illumination lights of different colors. An example of such light source may be configured to diffract a plurality of illumination lights of different colors emitted from a white light source and selectively emit the diffracted illumination lights.

Figure 9A:
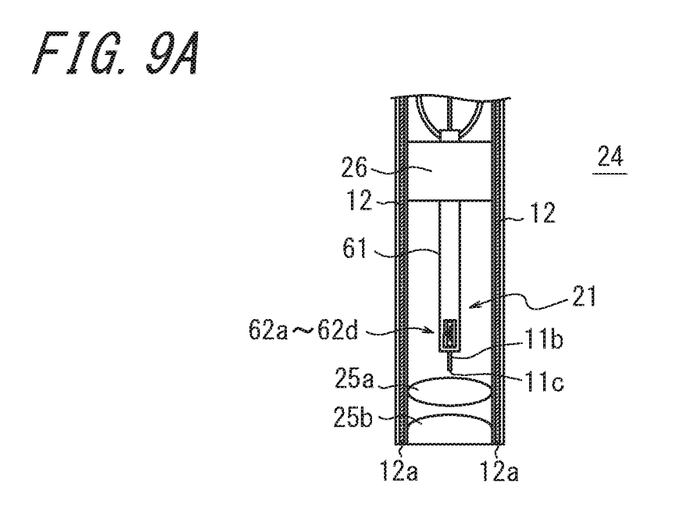
FIG. 9A is a sectional view of the tip part of the scope.
Figure 9B:
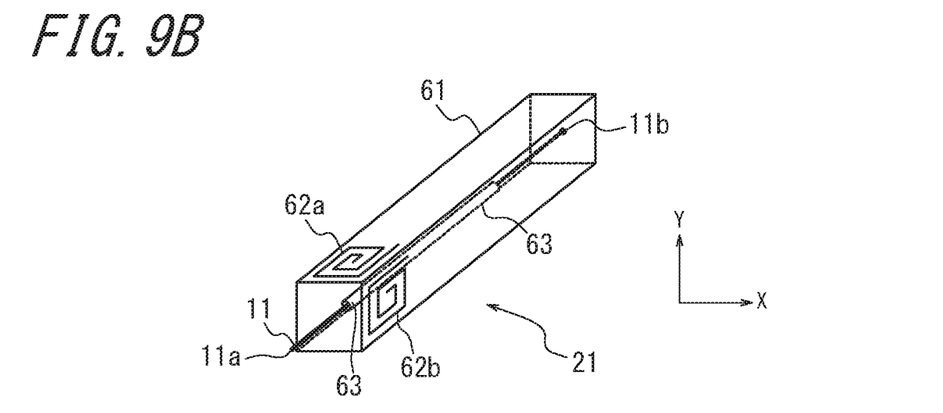
FIG. 9B is an enlarged perspective view of the actuator of FIG. 9A.
Figure 9C:
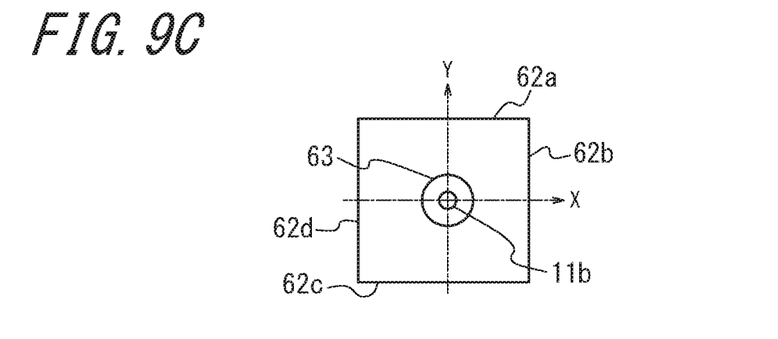
FIG. 9C is a sectional view of a portion including the deflecting magnetic field generating coils and the permanent magnet of FIG. 9B taken along a plane perpendicular to the axis of the optical fiber.

Further, in Embodiments 1 and 2, the actuator 21 of the illumination optical fiber 11 is not limited to the one using a piezoelectric elements, and may use, for example, a permanent magnet fixed to the illumination optical fiber 11 and a deflecting magnetic field generating coil (electromagnetic coil) for driving the permanent magnet. In below, a modified example of the actuator 21 is explained with reference to FIGS. 9A and 9B. FIG. 9A is a sectional view of the tip part 24 of the scope 20, FIG. 9B is an enlarged perspective view of the actuator 21 of FIG. 9A, and FIG. 9C is a sectional view of a portion including deflecting magnetic field generating coils 62a to 62d and a permanent magnet 63 of FIG. 9B taken along a plane perpendicular to the axis of the optical fiber 11.

The oscillation part 11b of the illumination optical fiber 11 is coupled, in part, with the permanent magnet 63 which is magnetized in the axial direction of the illumination optical fiber 11 and has a through hole, with the illumination optical fiber 11 penetrating the through hole. Further, an angular tube 61 fixed at one end thereof to the attachment ring 26 is disposed so as to surround the oscillation part 11b, and the angular tube 61 has deflecting magnetic field generating coils 62a to 62d of flat package type each disposed on respective side faces thereof in a region facing one of the magnetic poles of the permanent magnet 63.

The pair of the deflecting magnetic field generating coils 62a and 62c in the Y direction and the pair of the deflecting magnetic field generating coils 62b and 62d in the X direction are disposed on faces opposing to each other of the angular tube 61, in which a line connecting the center of the deflecting magnetic field generating coil 62a and the center of the deflecting magnetic field generating coil 62c and a line connecting the center of deflecting magnetic field generating coil 62b and the center of the deflecting magnetic field generating coil 62d intersect with each other at right angles near the central axis of the angular tube 61 where the illumination optical fiber 11 is disposed when stationary. The coils are connected, via the wiring cable 13, to the actuator 38 of the control device body 30 and driven by a drive current from the drive controller 38.

The disclosed optical scanning observation apparatus may also be applied to other optical scanning observation apparatus such as an optical scanning microscope, without being limited to the optical scanning endoscope apparatus.

REFERENCE SIGNS LIST 10 optical scanning endoscope apparatus
11 illumination optical fiber
11a fixed end
11b oscillation part
11c tip part
12 detection optical fiber bundle
13 wiring cable
20 scope
21 actuator
22 operation portion
23 insertion portion
24 tip part
25a, 25b projection lens
26 attachment ring
27 actuator tube
28a to 28d piezoelectric element
29 fiber holding member
30 control device body
31 controller
32 light emission timing controller
33 light source
33R, 33G, 33B laser
34 coupler
35 photodetector
36 ADC
37 signal processor
38 drive controller
40 display
61 angular tube
62a to 62d deflecting magnetic field generating coil
63 permanent magnet
70 object color detector
100 object

The invention claimed is:

1. An optical scanning observation apparatus for generating image signals for neighboring pixels, wherein the image signal of each of the neighboring pixels has components of a predetermined number of colors, the optical scanning observation apparatus comprising:
a light source configured to be controlled to sequentially emit illumination lights of the predetermined number of colors;
a fiber configured to guide the illumination lights emitted by the light source and to emit the illumination lights from a tip part of the fiber;
an actuator configured to drive the tip part of the fiber; along a scanning trajectory to scan the illumination lights emitted from the tip of the fiber on to an object;
a controller configured to,
for generating the image signals for the neighboring pixels, control a ratio of number of light emissions among the predetermined number of colors by the light source such that a number of light emission of a color having a higher contribution to image quality is set higher than a number of light emission of each color of the remaining colors of the predetermined number of colors having a lower contribution to image quality; and for a first pixel of the neighboring pixels, control the light source to sequentially emit illumination light of the color having the higher contribution to image quality and illumination light a first color of the remaining colors having the lower contribution to image quality; and for a second pixel of the neighboring pixels, control the light source to sequentially emit illumination light of the color having the higher contribution to image quality and illumination light of a second color of the remaining colors having the lower contribution to image quality, a photodetector configured to:
for the first pixel of the neighboring pixels:
convert detection light from the object scanned by the illumination light of the color having the higher contribution to image quality to a first color component signal for the first pixel; and
convert detection light from the object scanned by the illumination light of the first color of the remaining colors having the lower contribution to image quality to a second color component signal for the first pixel; and
for the second pixel of the neighboring pixels:
convert detection light from the object scanned by the illumination light of the color having the higher contribution to image quality to a first color component signal for the second pixel; and
convert detection light from the object scanned by the illumination light of the second color of the remaining colors having the lower contribution to image quality to a third color component signal for the second pixel; and a processor configured to:
generate an image signal for the first pixel of the neighboring pixels based on the first color component signal for the first pixel and the second color component signal for the first pixel;
generate an interpolated second color component signal, corresponding to the second color of the remaining colors having the lower contribution to image quality, for the second pixel based on interpolation of the image signal for the first pixel; and
generate an image signal for the second pixel of the neighboring pixels based on the first color component signal for the second pixel, the interpolated second color component signal for the second pixel and the third color component signal for the second pixel.

2. The optical scanning observation apparatus according to claim 1,
wherein the image quality comprises image brightness or contrast or bandwidth, or any combination thereof.

3. The optical scanning observation apparatus according to claim 1,
wherein the processor is configured to extract, from image signals of an arbitrary image, the color having the higher contribution to image quality.

4. The optical scanning observation apparatus according to claim 1,
wherein the controller is configured to control the ratio of the number of light emissions among the predetermined number of colors by the light source based on a user input received through in input device.

5. The optical scanning observation apparatus according to claim 1,
wherein the controller is configured to retrieve the ratio of the number of light emissions among the predetermined number of colors by the light source from a memory.

6. The optical scanning observation apparatus according to claim 1,
wherein the neighboring pixels are neighboring pixels along the scanning trajectory of the tip of the fiber.

7. The optical scanning observation apparatus according to claim 1,
wherein the neighboring pixels are neighboring pixels of an image to be output to a display.

8. A method for generating image signals for neighboring pixels, wherein the image signal of each of the neighboring pixels has components of a predetermined number of colors, the method comprising:

controlling a light source to sequentially emit illumination lights of the predetermined number of colors;

controlling an actuator to drive a tip of a fiber, wherein the fiber guides the illumination lights emitted by the light source and emits the illumination lights from the tip of the fiber, along a scanning trajectory to scan the illumination lights emitted from the tip of the fiber on to an object;

for generating the image signals for the neighboring pixels, controlling a ratio of number of light emissions among the predetermined number of colors by the light source such that a number of light emission of a color having a higher contribution to image quality is set higher than a number of light emission of each color of the remaining colors of the predetermined number of colors having a lower contribution to image quality;

for a first pixel of the neighboring pixels, controlling the light source to sequentially emit illumination light of the color having the higher contribution to image quality and illumination light a first color of the remaining colors having the lower contribution to image quality;

for a second pixel of the neighboring pixels, controlling the light source to sequentially emit illumination light of the color having the higher contribution to image quality and illumination light of a second color of the remaining colors having the lower contribution to image quality;

for the first pixel of the neighboring pixels:
converting detection light from the object scanned by the illumination light of the color having the higher contribution to image quality to a first color component signal for the first pixel; and
converting detection light from the object scanned by the illumination light of the first color of the remaining colors having the lower contribution to image quality to a second color component signal for the first pixel;

for the second pixel of the neighboring pixels:
converting detection light from the object scanned by the illumination light of the color having the higher contribution to image quality to a first color component signal for the second pixel; and
converting detection light from the object scanned by the illumination light of the second color of the remaining colors having the lower contribution to image quality to a third color component signal for the second pixel;

generating an image signal for the first pixel of the neighboring pixels based on the first color component signal for the first pixel and the second color component signal for the first pixel;

generating an interpolated second color component signal, corresponding to the second color of the remaining colors having the lower contribution to image quality, for the second pixel based on interpolation of the image signal for the first pixel; and generating an image signal for the second pixel of the neighboring pixels based on the first color component signal for the second pixel, the interpolated second color component signal for the second pixel and the third color component signal for the second pixel.

9. A non-transitory computer-readable storage device storing instructions that cause one or more processors to generate image signals for neighboring pixels, wherein the image signal of each of the neighboring pixels has components of a predetermined number of colors, the instructions causing the one or more processors to at least perform:

controlling a light source to sequentially emit illumination lights of the predetermined number of colors;

controlling an actuator to drive a tip of a fiber, wherein the fiber guides the illumination lights emitted by the light source and emits the illumination lights from the tip of the fiber, along a scanning trajectory to scan the illumination lights emitted from the tip of the fiber on to an object;

for generating the image signals for the neighboring pixels, controlling a ratio of number of light emissions among the predetermined number of colors by the light source such that a number of light emission of a color having a higher contribution to image quality is set higher than a number of light emission of each color of the remaining colors of the predetermined number of colors having a lower contribution to image quality;

for a first pixel of the neighboring pixels, controlling the light source to sequentially emit illumination light of the color having the higher contribution to image quality and illumination light a first color of the remaining colors having the lower contribution to image quality;

for a second pixel of the neighboring pixels, controlling the light source to sequentially emit illumination light of the color having the higher contribution to image quality and illumination light of a second color of the remaining colors having the lower contribution to image quality;

for the first pixel of the neighboring pixels:
converting detection light from the object scanned by the illumination light of the color having the higher contribution to image quality to a first color component signal for the first pixel; and
converting detection light from the object scanned by the illumination light of the first color of the remaining colors having the lower contribution to image quality to a second color component signal for the first pixel;

for the second pixel of the neighboring pixels:
converting detection light from the object scanned by the illumination light of the color having the higher contribution to image quality to a first color component signal for the second pixel; and
converting detection light from the object scanned by the illumination light of the second color of the remaining colors having the lower contribution to image quality to a third color component signal for the second pixel;

generating an image signal for the first pixel of the neighboring pixels based on the first color component signal for the first pixel and the second color component signal for the first pixel;

generating an interpolated second color component signal, corresponding to the second color of the remaining colors having the lower contribution to image quality, for the second pixel based on interpolation of the image signal for the first pixel; and generating an image signal for the second pixel of the neighboring pixels based on the first color component signal for the second pixel, the interpolated second color component signal for the second pixel and the third color component signal for the second pixel.

* * * * *